(12) United States Patent
Alemu et al.

(10) Patent No.: US 11,508,396 B2
(45) Date of Patent: Nov. 22, 2022

(54) ACQUIRING SPEECH FEATURES FOR PREDICTING EMOTIONAL SEVERITY OF ADVERSE EVENTS ON INDIVIDUALS

(71) Applicant: TQINTELLIGENCE, Inc., Atlanta, GA (US)

(72) Inventors: Yared Alemu, Atlanta, GA (US); Desmond Caulley, Lithonia, GA (US); Ashutosh A. Joshi, Atlanta, GA (US)

(73) Assignee: TQINTELLIGENCE, INC., Atlanta, GA (US)

( * ) Notice: Subject to any disclaimer, the term of this patent is extended or adjusted under 35 U.S.C. 154(b) by 0 days.

(21) Appl. No.: 17/550,544

(22) Filed: Dec. 14, 2021

(65) Prior Publication Data

US 2022/0189502 A1 Jun. 16, 2022

Related U.S. Application Data

(60) Provisional application No. 63/125,648, filed on Dec. 15, 2020.

(51) Int. Cl.
*G10L 25/63* (2013.01)
*G10L 15/16* (2006.01)

(52) U.S. Cl.
CPC .............. *G10L 25/63* (2013.01); *G10L 15/16* (2013.01)

(58) Field of Classification Search
CPC ................................ G10L 25/63; G10L 15/16
USPC ....................................................... 704/232
See application file for complete search history.

(56) References Cited

U.S. PATENT DOCUMENTS

| 2020/0302953 A1* | 9/2020 | Ando .................... G06N 20/00 |
| 2021/0192332 A1* | 6/2021 | Gangotri ................ G10L 15/16 |
| 2022/0059117 A1* | 2/2022 | Shor ...................... G10L 25/30 |

OTHER PUBLICATIONS

Latif, et al. "Deep Architecture Enhancing Robustness to Noise, Adversarial Attacks, and Cross-corpus Setting for Speech Emotion Recognition", Jul. 26, 2020, arXiv (Year: 2020).*

* cited by examiner

*Primary Examiner* — Pierre Louis Desir
*Assistant Examiner* — Nicole A K Schmieder
(74) *Attorney, Agent, or Firm* — Thomas | Horstemeyer, LLP

(57) ABSTRACT

Systems and methods of related to a voice-based system used to determine the severity of emotional distress within an audio recording of an individual is provided. In one non-limiting example, a system comprises a computing device that is configured to receive an audio sample that includes an utterance of a user. Feature extraction is performed on the audio sample to extract a plurality of acoustic emotion features using a base model. Emotion level predictions are generated for an emotion type based at least in part on the acoustic emotion features provided to an emotion specific model. An emotion classification for the audio sample is determined based on the emotion level predictions. The emotion classification comprises the emotion type and a level associated with the emotion type.

18 Claims, 11 Drawing Sheets

ACQUIRING SPEECH FEATURES FOR PREDICTING EMOTIONAL SEVERITY OF ADVERSE EVENTS ON INDIVIDUALS

CROSS-REFERENCE TO RELATED APPLICATIONS

This application is a claims priority to, and the benefit of, co-pending U.S. Provisional Application No. 63/125,648, filed on Dec. 15, 2020, entitled "SPEECH EMOTION RECOGNITION FOR CLASSIFYING EMOTIONAL DISTRESS SEVERITY," which is incorporated by reference in its entirety

BACKGROUND

Typically, a therapist will provide a diagnosis of a patient during a therapy session. The diagnosis will be based on the conversation conducted between the patient and the therapist. Over several sessions, the therapist will gauge the progress of the patient based on subsequent conversations.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1A:
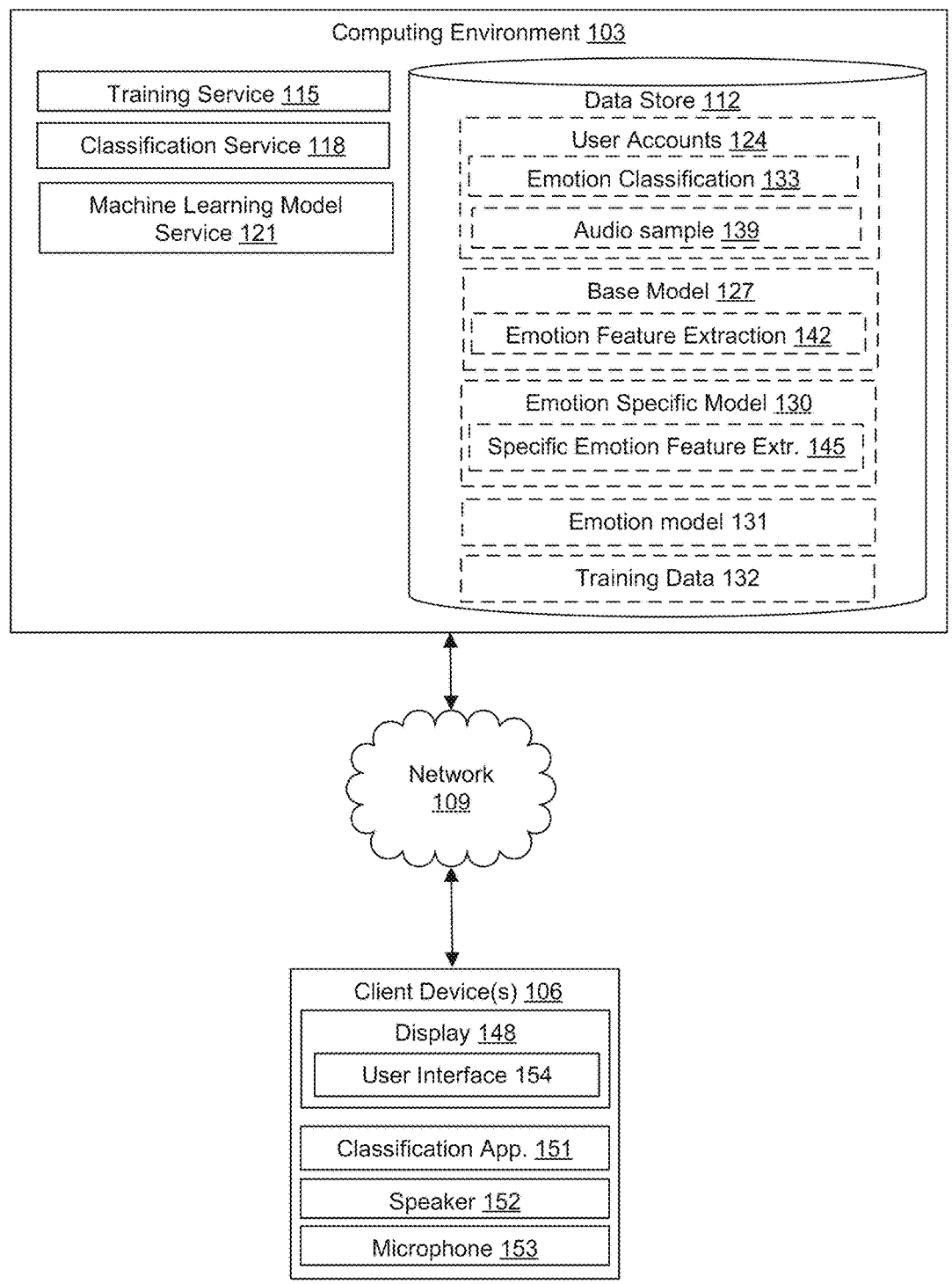
FIG. 1A is a drawing of a networked environment according to various embodiments of the present disclosure.

The present disclosure of the various embodiments relates to a voice-based system used to determine the severity of emotional distress within an individual using their audio recording. For example, the embodiments can be used to predict the emotional distress severity of children and adolescents who are in treatment for emotional/behavioral disturbances. During therapy, patients in these age groups routinely struggle with identifying and articulating their emotions. They can struggle with conversing about their emotional state. In fact, some individuals may even struggle revealing their emotions due to the lack of trust with any persons identified as an adult they consider having power over them. This lack of clarity on identifying emotions in the context of mental health treatment negatively impacts the effectiveness of mental health treatment. Thus, clinicians struggle to assess the effectiveness of therapy sessions and how to systemically evaluate treatments outcomes. There is no objective way to quantify how well the patients are doing. The present disclosure relates to providing systems and methods for analyzing the severity of the mental health conditions by focusing on emotional distress and/or negative emotions. Emotional distresses is a transdiagnostic process of measuring the severity of mental illness. All mental health conditions have an underlying emotional distress/negative emotion that determines the severity of the mental health condition, such as, for example, depressive or bipolar disorders.

In some embodiments, the present disclosures identify and use five main emotion types (e.g., anger, fear, happiness, sadness, neutral). For example, these emotions can be called archetypal emotions, similar to primary colors in which almost all other colors are derivatives. The archetypal emotions listed above can be a window into multiple other emotions. The measurement of these emotions can likely tap into a constellation of emotional experiences that accounts for the severity of the emotional distress and the level of the individuals' functional impairments as a result. Thus, rather than giving the individual a diagnosis for mental health disorders (e.g., anxiety disorder), the present disclosure relates to methods and systems to objectively identify and predict the underlying or the foundational emotional experiences.

Among all the biomarkers under development by researchers currently, speech stands out as an attractive candidate with features such as affordability, non-invasive, and non-intrusive. More specifically, pediatric trauma has a physiological link to changes in voice patterns (see e.g., FIG. 1B, 1C, and 1D). Trauma contributes to more than 80% of the mental health diagnosis for some population groups, such as children and adolescents. Youth that have a history of traumatic exposure show signs of attention span dysregulation (anger), distractibility (fear/sadness), and disorganized attachment (fear/anger/sadness).

Additionally, the various embodiments of the present disclosure can be applicable to a cohort of patients with various emotional/behavioral disorders from a variety of cultural and linguistic backgrounds. In some examples, this capability can be achieved by selecting prosodic and acoustic features commonly existing in human speech and predicting each individual's emotional distress and/or negative emotion. In some implementations, this speech clustering emotion can be assisted initially by traditional clinical diagnosis and at least three scientifically validated surveys, the Adverse Childhood Experiences (ACE), PHQ-9 (Patient Health Questionnaire 9), and Symptom and Functioning Severity Scale (SFSS).

Also, emotional states can have a temporal structure. For example, people with bipolar depression or chronic anxiety may be in such intense emotional states for months and years, or one may have a negative emotion for weeks and months. On the other hand, Anger and Excitement emotions may be transient and last for no more than a few minutes. Emotions, therefore, have a broad meaning and a narrow sense. Overall, the meaning reflects the long-term distress underlying it, and the narrow sense applies to the mental stimulation that motivates people to behave in the short term. To correctly identify the level of emotional distress, the embodiments of the present disclosure can identify the underlying emotions of the behavioral/emotional disorder severity.

The voice-based algorithm of the embodiments can be trained to understand behavioral and emotional tendencies and to anticipate future behaviors to determine if an individual's (e.g., a child's) vocal utterances deviate from age-appropriate linguistic and speech patterns. Improving long-standing outcomes disparities for individuals (e.g., youth from low-income communities) can require innovative approaches to measuring the severity of emotional distress and personalized treatment plans.

Thus, the embodiments of the present disclosure relate to various improvements for predicting emotional severity of adverse events experienced by individuals. For example, the embodiments of the present disclosure are directed to improved approaches that (1) train a machine learning base model to learn relevant emotional characteristics as feature extraction from an input audio; (2) train a downstream machine learning model to learn relevant emotion characteristics for a specific emotion type; (3) provide a prediction of emotional severity of adverse events on an individual, in which the prediction can include a combination of one or more basic emotional types; and other improvements that are described in the present disclosure. In the following discussion, a general description of the system and its components is provided, followed by a discussion of the operation of the same.

With reference to FIG. 1A, shown is a networked environment 100 according to various embodiments. The networked environment 100 includes a computing environment 103, and a client device 106, which are in data communication with each other via a network 109. The network 109 includes, for example, the Internet, intranets, extranets, wide area networks (WANs), local area networks (LANs), wired networks, wireless networks, or other suitable networks, etc., or any combination of two or more such networks. For example, such networks may comprise satellite networks, cable networks, Ethernet networks, and other types of networks.

The computing environment 103 may comprise, for example, a server computer or any other system providing computing capability. Alternatively, the computing environment 103 may employ a plurality of computing devices that may be arranged, for example, in one or more server banks or computer banks or other arrangements. Such computing devices may be in a single installation or may be distributed among many different geographical locations. For example, the computing environment 103 may include a plurality of computing devices that together may comprise a hosted computing resource, a grid computing resource and/or any other distributed computing arrangement. In some cases, the computing environment 103 may correspond to an elastic computing resource where the allotted capacity of processing, network, storage, or other computing-related resources may vary over time.

Various applications and/or other functionality may be executed in the computing environment 103 according to various embodiments. Also, various data is stored in a data store 112 that is accessible to the computing environment 103. The data store 112 may be representative of a plurality of data stores 112 as can be appreciated. The data stored in the data store 112, for example, is associated with the operation of the various applications and/or functional entities described below.

The components executed on the computing environment 103, for example, may include a training service 115, a classification service 118, a machine learning model service 121 and other applications, services, processes, systems, engines, or functionality not discussed in detail herein. The training service 115 can be executed to train machine learning models (e.g., which may be hosted in the machine learning model service 121) that are used to determine an emotional type and an emotional severity level based on an audio sample from a user (e.g., a therapy patient). In some embodiments, the training service 115 can train a base model for general (e.g., applicable for all emotion types) emotional feature extraction. The training service 115 can also be used to training an emotion-specific model. For example, the training service 115 can be used to train machine learning models that learns how to predict the level of emotion for a specific type of emotion (e.g., fear, happiness, sadness, anger, neutral etc).

The classification service 118 can be executed to predict an emotion level of an audio sample for one or more emotion categories (e.g., fear, happiness, sadness, anger, neutral etc.) using machine learning models that have been trained by the training service 115. The classification service 118 can work with a client application executed on the client device 106 to perform the emotion predictions. In some embodiments, the classification service 118 can generate an aggregate emotional score based on two or more categories. For example, an aggregate emotional score can be the average of the negative emotion categories (e.g., sadness, anger, fear, neutral) in order to represent a level of emotional trauma represented in the audio sample.

The data stored in the data store 112 includes, for example, user accounts 124, a base model 127, an emotion specific models 130, an emotion model 131, training data 132, and potentially other data. The user accounts 124 represent an individual user profile or account for everyone being evaluated for an emotion diagnosis. The user accounts 124 can include an emotion classification 133, and emotion severity level 136, an audio sample 139, and other suitable data.

The emotion classification 133 can represent one or more emotion classification generated for an audio sample 139 of a user. The emotion classification 133 can indicate a level of emotional trauma experienced by an individual. For example, the emotional trauma can exist because of adverse events experienced by the individual. In some examples, the emotion classification 133 can include a classification for different emotions (e.g., happiness, anger, fear, sadness, neutral (when all emotions are classified as in the low range)). For instance, a non-limiting example of an emotion classification 133 of an audio sample 139 can include a medium level for sadness, a high level for anger, a medium level for fear, and a low level for happiness. In some implementations, the emotion classification 133 can represent one or more emotion types that are predicted.

The audio sample 139 can represent audio captured of the user (e.g., a patient). The audio sample 139 can be captured by the client device 106. The user can be asked to recite a defined set of statements for the audio sample 139.

The base model 127 can represent a model used for feature extraction of general emotion characteristics from an audio sample 139 or from training data 132. The base model 127 can perform feature extraction for one or more emotion specific models 130. The emotion feature extraction 142 can represent acoustic emotion characteristics that are extracted from the audio sample 139 or the training data 132. In some embodiments, the emotion feature extraction 142 can be a set of vectors that characterize a portion of the audio input.

The base model 127 can also include data learned from training data 132 or a series of audio samples 139. The learned data can be used to optimize the base model 127. Some non-limiting examples of values learned can include filter values for convolution neutral network (CNN) layers, values for Densenet-style layers, values for a transformer layer, and other suitable values for optimizing the base model 127. The base model 127 can perform feature extractions for one or more emotion specific models 130.

The emotion specific model 130 (e.g., a sadness model, an anger model, a happiness model, a fear model, and a neutral model) can represent a model that is trained to predict a level of a specific emotions existing in the audio sample 139 or in the training data 132. For example, an anger specific model can determine whether an audio sample should be classified as having a low, medium, or a high level for the anger emotion. The emotion specific model 130 can include specific emotion feature extractions 145, which can represent emotion specific acoustic characteristics that are identified or learned.

For instance, the anger emotion specific model 130 learns acoustic characteristics that are relevant for classifying the level of anger in an audio sample 139 or in training data 132. Likewise, the emotion specific model 130 for sadness, happiness, and fear can learn acoustic features that are relevant for each specific emotion. Some non-limiting examples of emotion characteristics for anger or happiness may include inter-word silence, pitch, tone, word emphasis, energy values, and other suitable emotional characteristics. The emotion specific model 130 may learn other specific emotion characteristics for other emotion types (e.g., sadness, fear).

The emotion model 131 can represent one or more models that are trained to predict a level of one or more emotion types existing in the audio sample 139 or in training data 132. In some embodiments, the emotion model 131 can include the base model 127 and one or more emotion specific models 130 downstream from the base model 127.

The training data 132 can represent audio datasets that are used for training the base model 127, the emotion model 131, and/or the emotion specific model 130. Each audio file can include a label for supervised learning for the machine learning models (e.g., the emotion model 131, and/or the emotion specific model 130). For example, the label can include a level that describes the level of a specific emotion type. For instance, one audio file can include a label that indicates a low level of anger is represented in the audio file. The label can be used for correcting and/or optimizing parameters in the machine learning models.

The client device 106 is representative of a plurality of client devices that may be coupled to the network 109. The client device 106 may comprise, for example, a processor-based system such as a computer system. Such a computer system may be embodied in the form of a desktop computer, a laptop computer, personal digital assistants, cellular telephones, smartphones, set-top boxes, music players, web pads, tablet computer systems, game consoles, electronic book readers, or other devices with like capability. The client device 106 may include a display 148. The display 148 may comprise, for example, one or more devices such as liquid crystal display (LCD) displays, gas plasma-based flat panel displays, organic light emitting diode (OLED) displays, electrophoretic ink (E ink) displays, LCD projectors, or other types of display devices, etc. The client device 106 can also include a speaker 152 and a microphone 153.

The client device 106 may be configured to execute various applications such as a classification application 151 and/or other applications. The classification application 151 can be executed to generate an emotion classification 133 for an audio sample 139. In some implementations, the classification application 151 can communicate with the classification service 118 in order to generate the emotion classification 133. In other implementations, the classification application 151 can generate the emotion classification 133 by executing one or more trained machine learning models executed on the client device 106.

The classification application 151 may also be executed in a client device 106, for example, to access network content served up by the computing environment 103 and/or other servers, thereby rendering a user interface 154 on the display 148. To this end, the classification application 151 may comprise, for example, a browser, a dedicated application, etc., and the user interface 154 may comprise a network page, an application screen, etc. The client device 106 may be configured to execute applications beyond the classification application 151 such as, for example, email applications, social networking applications, word processors, spreadsheets, and/or other applications.

Next, a general description of the operation of the various components of the networked environment 100 is provided. To begin, the embodiments can be used in various scenarios for predicting different types of emotions from an audio sample 139 of an individual. First, one or more machine learning models can be trained as the base model 127. The base model 127 is meant to learn general emotion related features (e.g., acoustic emotion characteristics) from raw audio of the training data 132. The training can occur in an unsupervised manner.

Next, one or more machine learning models can be trained as emotion specific models 130 for a specific emotion type, such as anger, sadness, happiness, fear, and other suitable emotions. In some examples, the emotion specific models 130 are trained in a supervised manner in order for the models to learn different levels of each emotion. For example, a fear emotion specific model 130 can predict a low, medium, or high level of fear of a provided audio sample 139.

In some implementations, the emotion specific model 130 can be provided as an input of features from the base model 127 in order to generate a prediction for a level of emotion in the audio sample 139. Thus, an emotion model 131 can be represented as using a combination of the base model 127 and the emotion specific model 130. The emotion model 131 can be executed in the classification service 118 and/or in the classification application 151.

In one non-limiting example, a therapist can have a client device 106 (e.g., a mobile phone) that executes the classification application 151. The classification application 151 can capture an audio sample 139 of a patient, such as a youth seeking therapy after experiencing a traumatic event. The patient may read a written script for the audio sample 139 capture. The classification application 151 can execute the emotion model 131 to generate the emotion classification 133. The emotion classification 133 can include a high level of sadness, a high level of fear, and low level of anger. In some examples, an aggregate score can be generated by averaging these three categories. The classification application 151 can store the emotion classification 133 in association with a particular day and time for a user account 124 of the patient. In subsequent sessions with the patient, the therapist can generate an additional emotion classification 133 in order to gauge whether the emotional distress is lowering. The trends of the emotion classification 133 can be useful for gauging whether a particular therapy technique is effective with the patient.

Figure 1B:
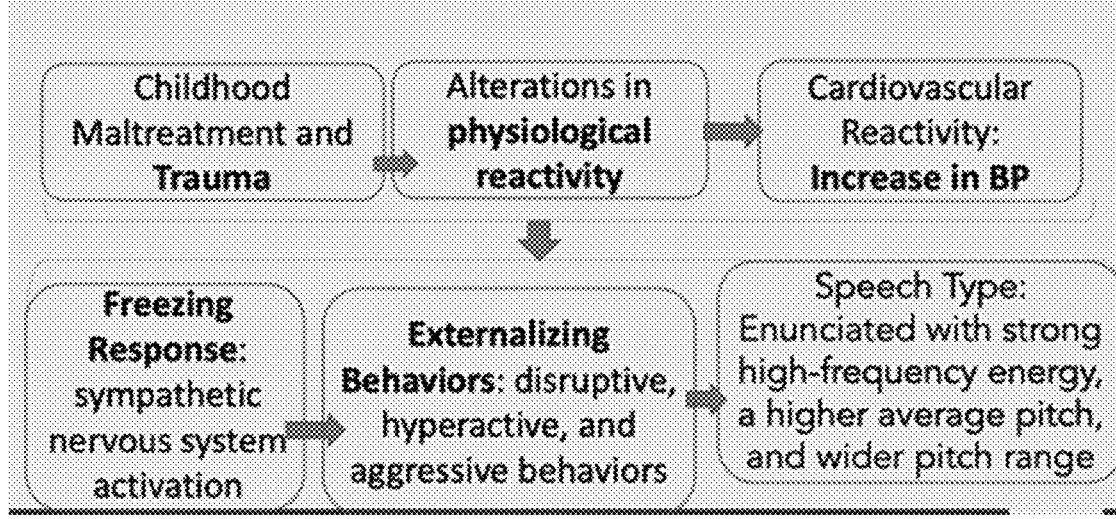
FIGS. 1B-1D are drawings illustrating a link between trauma, cardiovascular activity, and voice types according to various embodiments of the present disclosure.
Figure 1C:
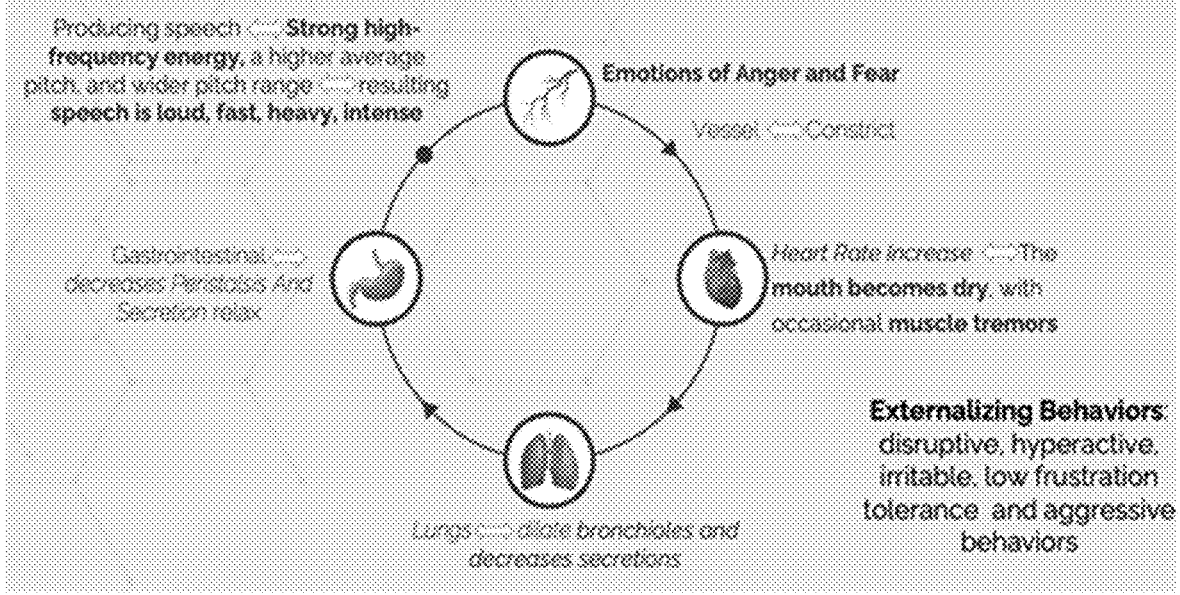
Figure 1D:
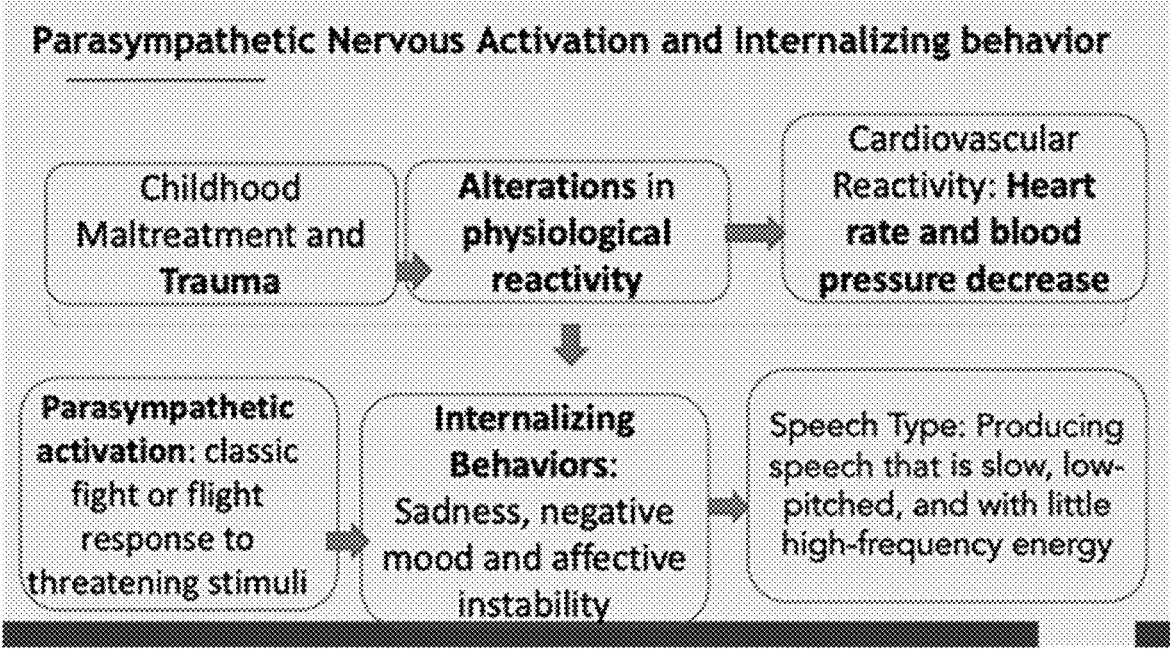

Referring next to FIGS. 1B-1D, shown are drawings related to one non-limiting embodiment for executing the emotion model 131 (e.g., executed in the computing environment 103 or in the client device 106) in a use case scenario for predicting a level of emotional trauma experienced by youth (e.g., children and adolescent). Regarding this use case scenario, FIGS. 1B-1D illustrate a link between trauma, cardiovascular activity, and voice types. The link between trauma/stress and voice types is related to the Automatic nervous system changes, including the disruption of speech-based characteristics, partly due to muscle tensions. Further, evidence exists, for example, of a correlation between neural activity in the gamma-aminobutyric acid (GABA) neurotransmitter, susceptibility to depression, and changes in muscle tonality. These changes related to muscle tonality can produce distinct utterances indicating the presence of negative mood/depressive symptoms, which can be linked to negative emotions (e.g., anger, sadness, fear). As such, the embodiments can be configured to predict a level of emotional trauma experienced by a child or adolescent.

Figure 2A:
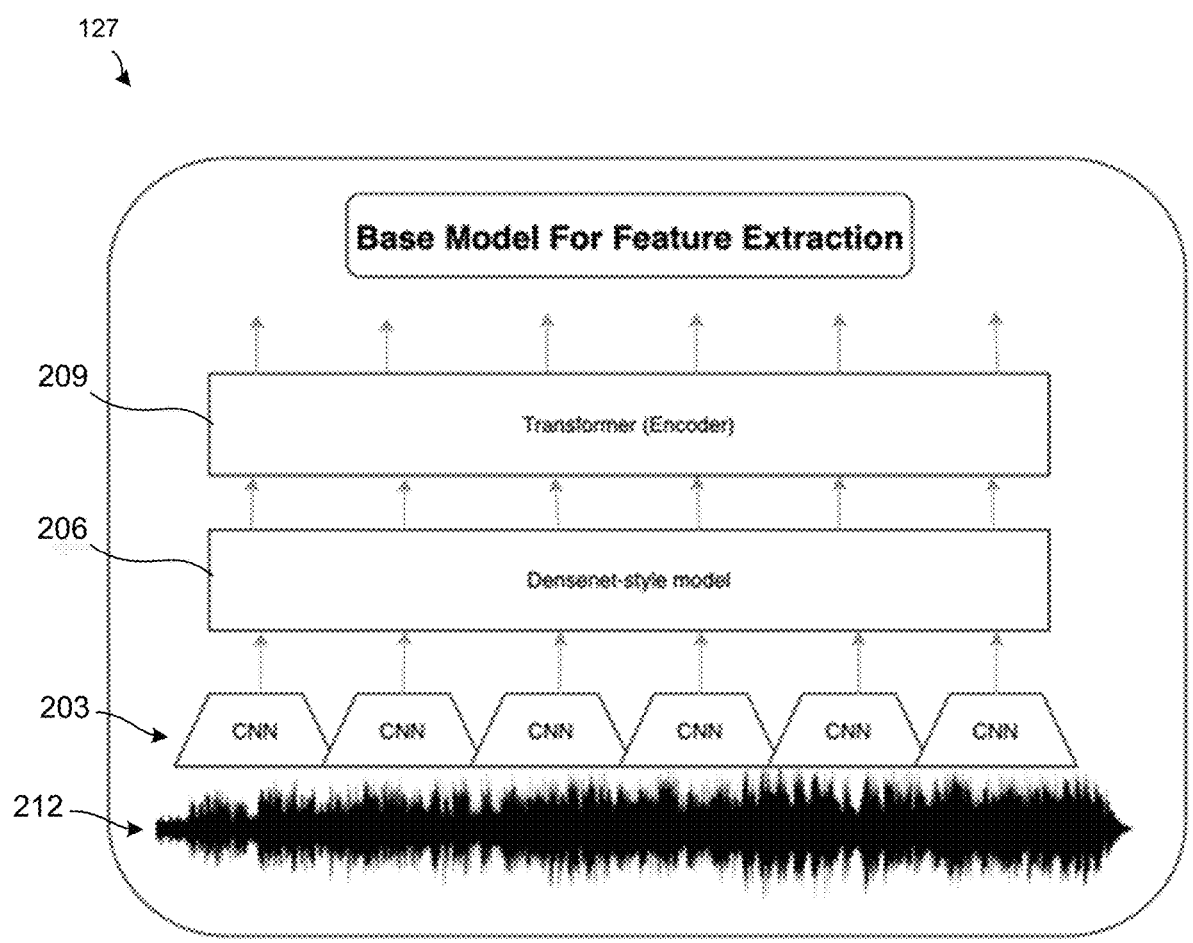
FIG. 2A is a drawing of portions of a base model in the networked environment of FIG. 1A according to various embodiments of the present disclosure.

Referring next to FIG. 2A, shown is drawing of an example of the base model 127. The base model 127 can be used to perform feature extraction on raw audio (e.g., from an audio sample 139 or from training data 132). The base model 127 can include a convolution neutral network 203 ("CNN 203"), a densenet model 206 (or a densenet-style model), a transformer layer 209 (e.g., an encoder), and other suitable components.

In one embodiment, the first step in a system can be a baseline (e.g., a base model 127), which can learn general emotion related features. In situations where there is not enough data from a target demographic, it can be relevant to learn initial representations from a larger dataset. This can be referred to as transfer learning. Thus, extracting features from the base model 127 allows for the embodiment to realize the power of transfer learning with a limited amount of data from our target population. The base model 127 can learn power representations on arbitrary data, and the base model 127 can be finetuned with subsequent data (e.g., from a targeted population).

In one non-limiting implementation, a source of the outside data was YouTube. Audio scraping methods can be built to acquire this data on human speech/emotion from YouTube. In some other implementations, a publicly available dataset that can be used to train feature extraction from the base model 127 is the AudioSet dataset, which is a collection of audio video segments obtained by Google®. In some non-limiting examples, the subset of AudioSet dataset that contains human speech and emotion can be sufficient for training the base model 127.

Typically, training a robust machine learning model requires a huge amount of labeled data which can be expensive and challenging to obtain particularly from a target demographic, such as, for example, individuals with adverse childhood events. Due to label constraints, the base model 127 can be trained in an unsupervised way. With any machine learning, a metric can be developed that allows the model to learn effectively (e.g., developing an effective loss function and back propagation strategy). Semantic-based tasks (e.g., Speech-to-texts) can rely on the rapid evolution of the specific aspect of speech used to convey meaning. Non-semantic tasks like emotion recognition, however, can evolve a lot more slowly. As a result, the base model 127 can be trained to use temporal proximity as a metric for evaluating the loss function of the system (e.g., the base model 127). In one example, the base model 127 can be trained to use temporal proximity through a triplet loss formulation.

As shown in FIG. 2A, the input audio 212 (e.g., raw audio of an audio sample 139 or training data 132) can be provided to the CNN 203. The CNN 203 can represent one or more CNN layers that form a CNN stack (e.g., see FIG. 2C).

Unlike existing models that directly compute acoustic features to pass into a CNN network, the embodiments can be configured to learn what those features are automatically. Previous work has used handcrafted features like the logarithmic Mel Spectrogram or the Mel Frequency Cepstral coefficients as the input to the CNN network. Instead of passing in those features, the goal of the CNN layer stack (e.g., CNN 203) is to learn those structures in the audio automatically.(e.g., of the input audio 212). In some non-limiting examples, the number of CNN 203 layers in the stack can vary between 2 and 10. In one non-limiting implementation, the number of filters of the first layer of the CNN 203 can be 512 with a kernel 320 with a stride of 160. This assumes that speech is stationary over a 20 ms chunk. For audio sampled at 16 KHz, this amounts to 320 samples. Each of the filters in the 512 kernels can be meant to function as a frequency bin filter. Subsequent layers in the CNN network 203 can learn higher level information about the structures in the speech. This includes but is not limited to cepstral structures or lower-level descriptors like energy. The output of the CNN 203 can be a series of vectors, in which each vector can individually represent a portion of the input audio 212.

With regard to the loss function, the output of the CNN 203 can serve as the input when calculating the loss function. Considering a set of features $X=x_1, x_2, \ldots x_T$ is obtained with each stride, the goal is to learn a model, $g$, where for $|t-m|>=|t-n|$ then $|g(x_t)-g(x_m)|>=|g(x_t)-g(x_n)|$. With this objective, the embodiments are minimizing the loss between points that are closer together while maximizing the loss for points that are extremely far away. This is a triplet loss formulation and at each step we need to select triplet examples of the form $(z_t, z_n, z_m)$.

Figure 2B:
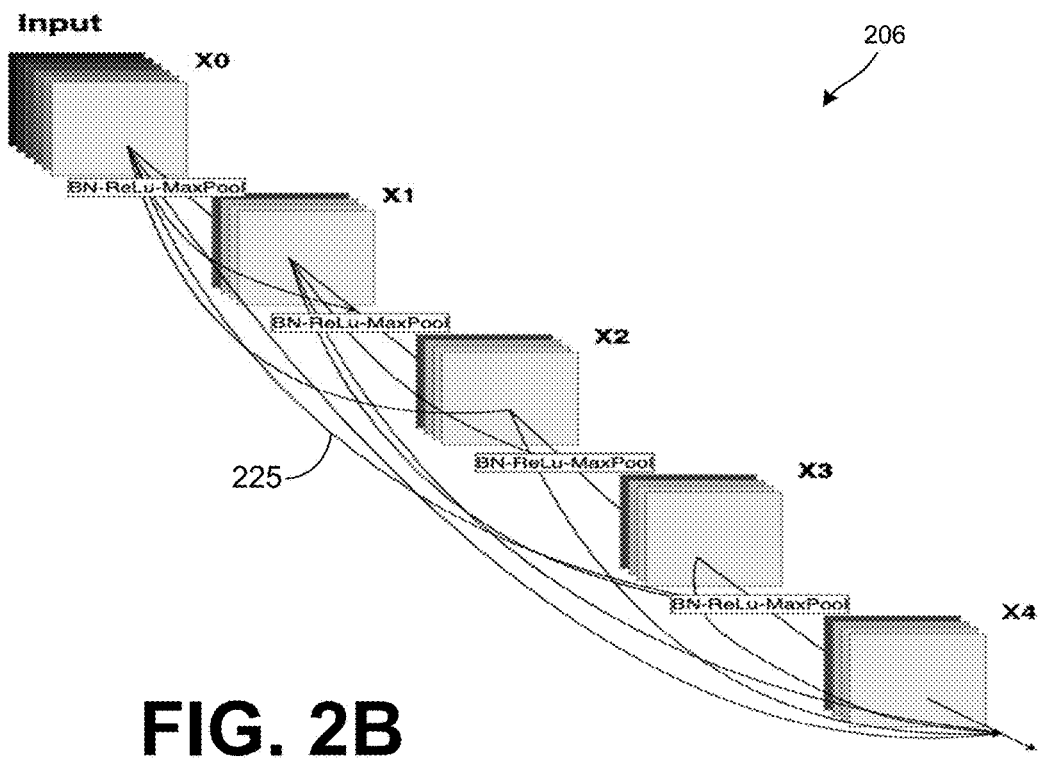
FIG. 2B is a drawing of portion of a Densenet model from the base model of FIG. 2A according to various embodiments of the present disclosure.

The output of the CNN 203 can be fed into the Densenet model 206, which is shown in FIG. 2B. Considering the base model 127 can be complex with many layers (e.g., CNN layers), there is the risk that the performance of the base model 127 suffers partly due to diminishing/exploding gradients. A deep network with a large number of parameters could lead to overfitting. In one non-limiting example, one way to avoid this degradation problem can be to implement skip connections 225 in a ResNet/Densenet model 206. Reference number 225 points to one of several possible skip connections illustrated in FIG. 2B. B. In many ways, the ResNet/Densenet model 206 can function like a gating mechanism of a long short-term memory (LSTM) model.

One unique aspect of the Densenet model 206 is that, once the features in lower levels that work extremely well have been identified, those features can be passed up to higher layers using the skip connections 225. What features get passed up to higher layer levels is learned by the network through backpropagation. In one non-limiting example, the Densenet model 206 can allow the model to learn features at various levels and pass important features down the line.

Figure 2C:
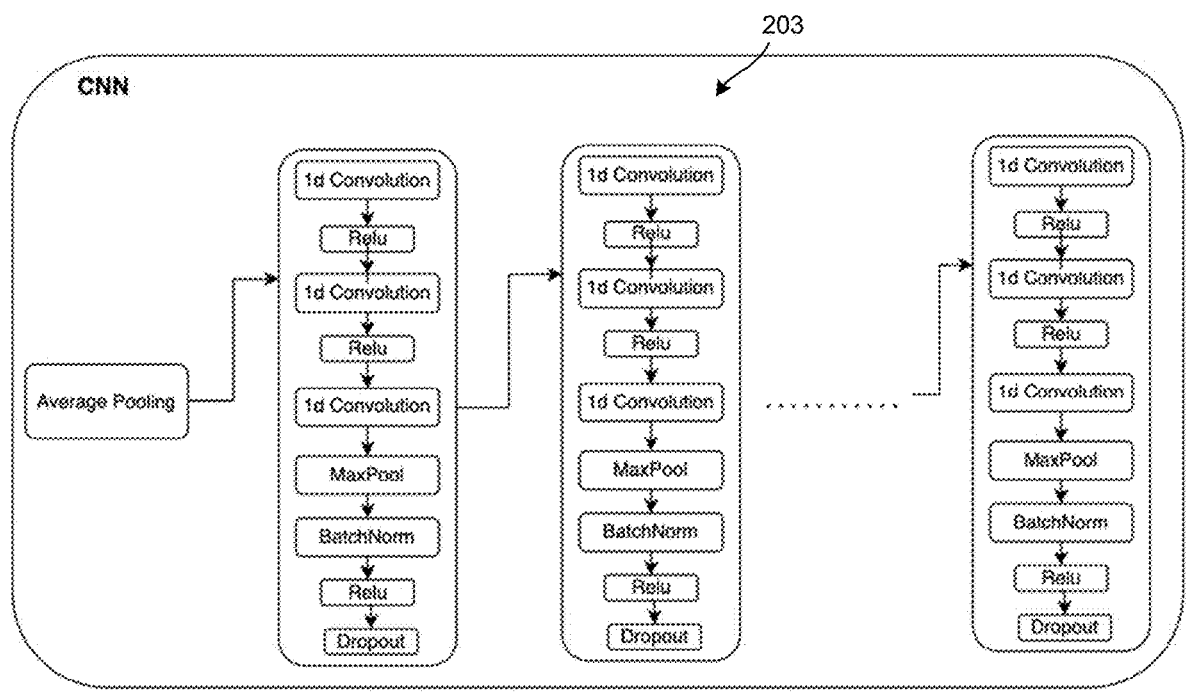
FIG. 2C is a drawing of a convolution neutral network from FIG. 2A according to various embodiments of the present disclosure.

The densenet model 206 generates an output of vectors that are provided to the transformer layer 209. The transformer layer 209 can be useful because it allows the base model 127 to learn relations between all the various parts of the utterance (e.g., the input audio 212). Specifically, it allows the base model 127 to learn how a sub-utterance at time t+k or t−k impacts an utterance at time t. The transformer layer 209 can operate as an attention mechanism and weigh the significance of various parts of the input utterance (e.g., the input audio 212). For example, one way this could be beneficial is that if a particular emotion is detected at utterance t of the input audio 212, it will be useful to identify other segments of the input audio 212 that verify this discovery at time t. Thus, the transformer layer 209 can allow the base model 127 to discover and properly weigh these other aspects of the audio when processing the sub-utterance at time t. The attention mechanism can work with a query, and key pair to obtain a particular value which is meaningful. FIG. 2C illustrates an example of the CNN layer 203 for the base model 127. The number of layers in the CNN 203 can vary.

Figure 3:
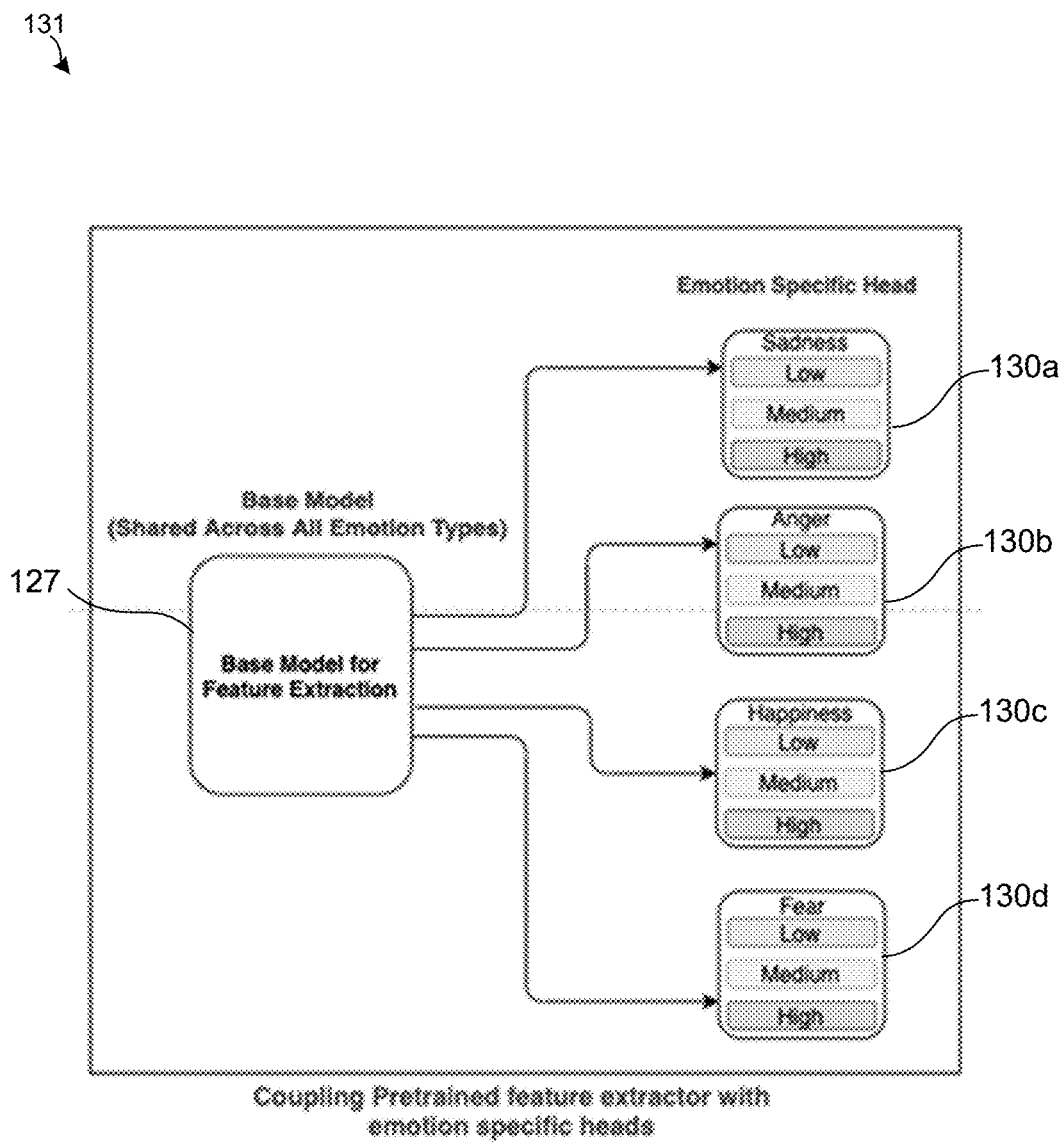
FIG. 3 is a drawing of another portion of a classification service in the networked environment of FIG. 1A according to various embodiments of the present disclosure.

Turning now to FIG. 3, shown is a drawing of an example of the emotion model 131. As previous described, the emotion model 131 can include the base model 127 and one or more emotion specific models 130a-130d (collectively "the emotion specific models 130"). In the illustrated example of FIG. 3, there is a separate emotion specific model 130 for anger, happiness, sadness, and fear. In this embodiment, the base model 127 has been trained for feature extraction of general acoustic emotions. The base model 127 can provide the extracted features to each of the emotion specific models 130. Each emotion specific model 130 can generate a prediction of a level of the degree of its specific emotion in the audio sample 139 or training data 132.

For example, the fear emotion specific model 130d can generate a prediction of the following: a twenty percent probability that there is a low level of fear, a thirty percent probability that there is a medium level of fear, and a fifty percent probability that there is a high level of fear. Since the high level of fear has the best probability, the fear emotion specific model 130d can select the audio sample 139 has a high level of fear. Additionally, the happiness emotion specific model 130c can generate a probability prediction for each level and select low level because it has the highest probability. In this example, the anger emotion specific model 130b can select a medium level because it has the highest probabilities and the sadness emotion specific model 130a can select the medium level as well. In some embodiments, the emotion model 131 can aggregate all or some of the scores. For example, the emotion model 131 can be used to predict the severity of emotional trauma experience in youth. The emotion model 131 can be configured to aggregate the negative emotions associated with the trauma, such as sadness, anger, and fear. Thus, the emotion model 131 can aggregate (e.g., taking an average) the medium level from anger, the medium level from the sadness, and the high level from fear. The average of these three levels can be computed to be a medium level as the aggregated score.

The training service 115 can be executed to train the emotion model 131. In some embodiments, the emotion model 131 can be trained in a supervised manner. The training data 132 can include audio dataset of audio files that have labels. The labels can correspond to different levels (e.g., low, medium, or high) or different degrees (e.g., a range between 0 percent to 100 percent) for classifying the audio file. For example, a first audio file can be labeled with low level of fear, low level of anger, low level of sadness, and high level of happiness. The first audio file can be inputted into the emotion model 131 and the emotion model 131 can generate level predictions for each emotion specific model 130. If the level prediction is wrong, then the emotion specific model 130 can be adjusted in order to optimize the predictions for subsequent audio files.

For instance, continuing with the previous example, the anger emotion specific model 130b can predict a high level of anger in the first audio file. The anger emotion specific model 130b can be optimized since the first audio file is labeled with a low level of anger. The training service 115 can supervise the training of the emotion model 131 by evaluating certain metrics for the emotion specific models 130.

Figure 4:
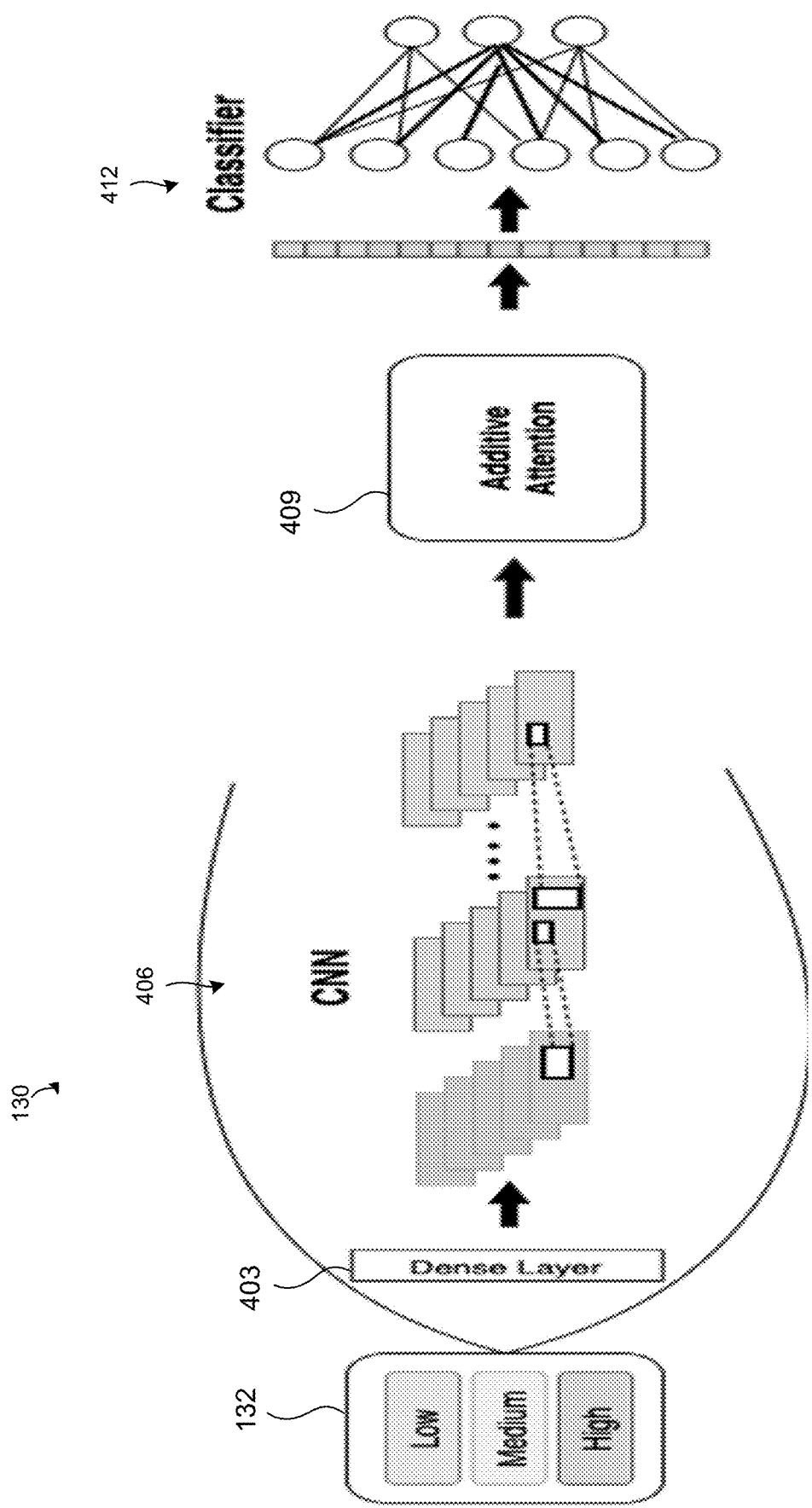
FIG. 4 is a drawing of another portion of a classification service in the networked environment of FIG. 1A according to various embodiments of the present disclosure.

Moving on to FIG. 4, shown is a drawing of an example of an emotion specific model 130. As shown in the illustrated example, the emotion specific model 130 can include a dense layer 403, a CNN layer 406 (see e.g., FIG. 2C), an additive attention layer 409, a classifier layer 412, and other suitable components.

The dense layer 403 can be used to reduce the dimensionality of the vector. In the emotion specific model 130, the CNN layer 406 can be used to learn emotion specific features. For example, we expect the CNN layer for the anger specific model to learn regions of lower pitch, higher intensity, higher first format, faster speech onset, and/or significant energy across vocalization. If all the aforementioned regions exist in an audio sample, then the subsequent classifier layer labels the audio sample as "high."

The additive attention layer 409 can be used to identify regions in an audio segment where an individual is expressing a particular emotion. We give these regions higher weights before classification. The classifier layer 412 can be used to generate a probability for each of the output labels. The output labels are normalized using a softmax layer.

In the illustrated example, the training data 132 can be inputted into the dense layer 403. The inputted audio files can have a label, such as high, medium, or low, for each emotion type (e.g., anger, sadness, happiness, fear). In some embodiments, the dense layer 403 can be omitted.

Figure 5:
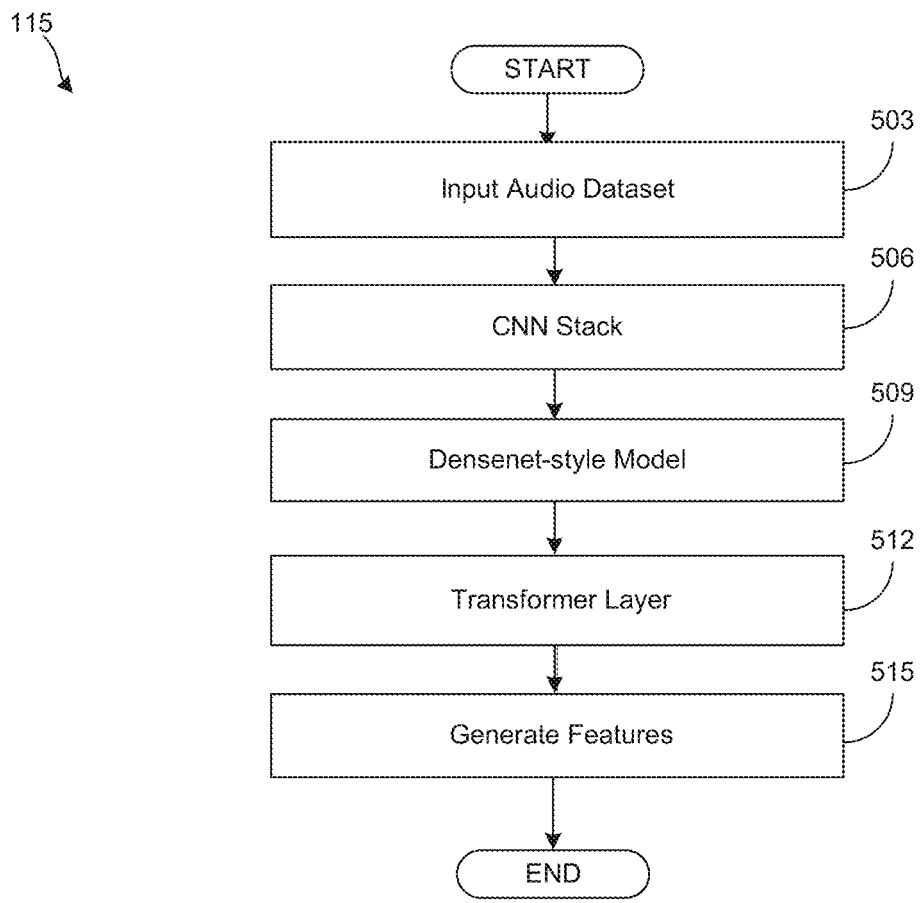
FIG. 5 is a flowchart illustrating one example of a training service implemented for training a base emotional model in a computing environment in the networked environment of FIG. 1A according to various embodiments of the present disclosure.

Referring next to FIG. 5, shown is a flowchart that provides one example of the operation of a portion of the training service 115 according to various embodiments. FIG. 5 illustrates an example of training the base model 127. It is understood that the flowchart of FIG. 5 provides merely an example of the many different types of functional arrangements that may be employed to implement the operation of the portion of the training service 115 as described herein. As an alternative, the flowchart of FIG. 5 may be viewed as depicting an example of elements of a method implemented in the computing environment 103 (FIG. 1A) according to one or more embodiments.

Beginning with box 503, the training service 115 can provide input audio 212 from an audio dataset (e.g., training data 132) to the CNN 203 in order to generate or extract features from the input audio 212.

In box 506, the training service 115 can cause the CNN 203 to generate or extract features from the input audio 212.

The extracted features can represent acoustic characteristics that describe the input audio 212. In some embodiments, the CNN 203 provides an output of vectors, in which each vector can correspond to a portion of the input audio. The training service 115 can cause the output of the CNN 203 to be provided to the Densenet model 206.

In box 509, the training service 115 can cause the Densenet model 206 to process the output from the CNN 203. The Densenet model 206 can be executed to prevent the performance of the model suffering partly due to diminishing/exploding gradients. In some embodiments, the skip connections 225 are implemented in the Densenet model 206. Skip connections 225 can skip some layers in the CNN 203 and can feed the output of one layer as the input to the next layers (e.g., instead of only the next one). The Densenet model 206 can produce a set of vectors as output that are fed to the transformer layer 209.

In box 512, the training service 115 can cause the transformer layer 209 to process the output from the Densenet model 206. The transformer layer 209 can generate data that describes relations between various parts of the input audio 212. The transformer layer 209 can determine how a sub-utterance at time t+k or t−k impacts an utterance at time t. The transformer layer 209 can act as an attention mechanism and weigh the significance of various parts of the input utterance. One way this could be beneficial is that if a particular emotion is detected at utterance t, it will be useful to identify other segments of the input audio that verifies this discovery at time t. A transformer layer 209 can allow us to discover and properly weigh these other aspects of the audio when processing the sub-utterance at time t. An attention mechanism works with a query, key pair to obtain a particular value which is meaningful. The attention mechanism can be used to identify the most relevant part (e.g., vector) of the input vectors from the Densenet model 206.

In box 515, the training service 115 can identify a set of features extracted from the base model 127. The extracted features can be a set of vectors (e.g., acoustic features) that describe emotion characteristics. Then, the training service 115 can proceed to completion.

Figure 6:
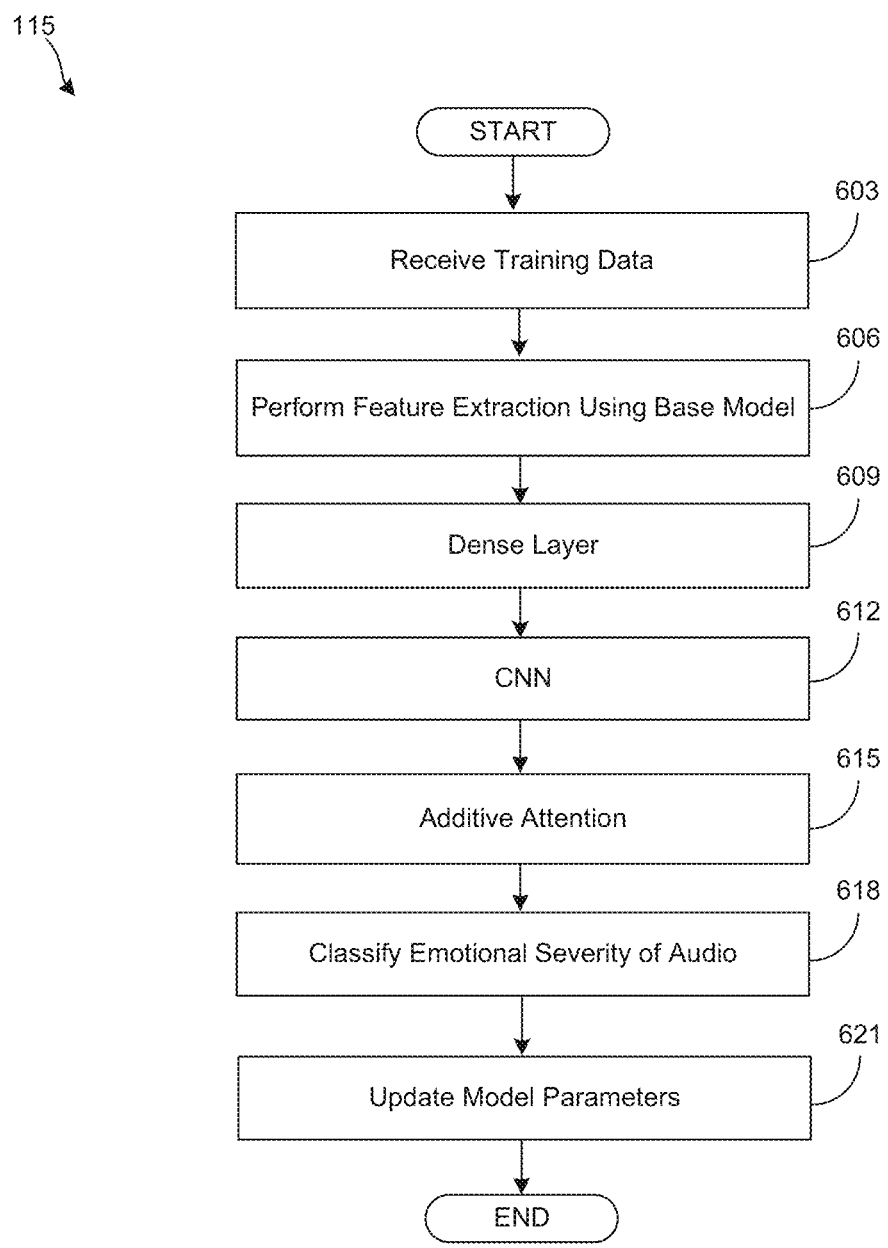
FIG. 6 is a flowchart illustrating one example of a training service implemented for training an emotional model in a computing environment in the networked environment of FIG. 1A according to various embodiments of the present disclosure.

Referring next to FIG. 6, shown is a flowchart that provides one example of the operation of a portion of the training service 115 according to various embodiments. FIG. 6 illustrates an example of training the emotion specific model 130. It is understood that the flowchart of FIG. 6 provides merely an example of the many different types of functional arrangements that may be employed to implement the operation of the portion of the training service 115 as described herein. As an alternative, the flowchart of FIG. 6 may be viewed as depicting an example of elements of a method implemented in the computing environment 103 (FIG. 1A) according to one or more embodiments.

Beginning with box 603, the training service 115 can provide input audio 212 from an audio dataset (e.g., training data 132) to the CNN 203 in order to generate or extract features from the input audio 212. In some embodiments, each input audio 212 can be have a label (e.g., low anger, medium happiness, etc.). The label can be used for supervised training, in which the prediction from the emotion model 131 can be compared to the label.

In box 606, the training service 115 can cause the base model 127 (e.g., via the emotion model 131) to perform feature extraction on the input audio 212. In this example, the base model 127 has been trained to extract acoustic emotion characteristics from the input audio 212. The output of the base model 127 can be provided to a dense layer 403.

In box 609, the training service 115 can cause the dense layer 403 to process the output of extracted features from the base model 127. The dense layer 403 process the extracted features in order to reduce dimensionality. The dense layer 403 can provide an output that is inputted to the CNN layer 406. In some embodiments, box 609 can be omitted. In these embodiments, the output of the base model 127 can be directed to the CNN layer 406.

In box 612, the training service 115 can cause the CNN layer 406 to process the output of the dense layer 403. The CNN layer 406 can generate an output that is provided to the additive attention layer 409.

In box 615, the training service 115 can cause the additive attention layer 409 to process the output from the CNN layer 409. The additive attention layer 409 can generate an output that is provided to the classifier layer 412.

In box 618, the training service 115 can cause the classifier layer 412 to generate a prediction for a level of emotion existing in the audio sample 139. In some embodiments, the classifier layer 412 can generate a prediction probability for each level (e.g., low, medium, high) of an emotion type (e.g., anger, fear, sadness, happiness). The classifier layer 412 can select the level that has the highest prediction probability for each emotion type. Further, in some examples, the classification service 118 can aggregate (e.g., an average) the levels (e.g., scores) for two or more emotion types.

In box 621, the training service 115 can cause the emotion specific model 130 to compare the prediction with the label for the input audio 212. For example, if the prediction is wrong (e.g., the predicted level does not match the level set for the input audio 212), the emotion specific model 130 can adjust parameters in the CNN layer 406 in order to tune for subsequent predictions. For example, the input audio 212 may have a label that indicates a low level for sadness. The predicted level may be computed to be a high level. By identifying that the high level and the low level do not match, the training service 115 can update one or more model parameters associated with the emotion specific model 130. Some non-limiting examples of adjustable parameters for the CNN can include the number of output channels, the stride, padding, kernel size, and other suitable parameters. Then, the training service 115 can proceed to completion.

Figure 7:
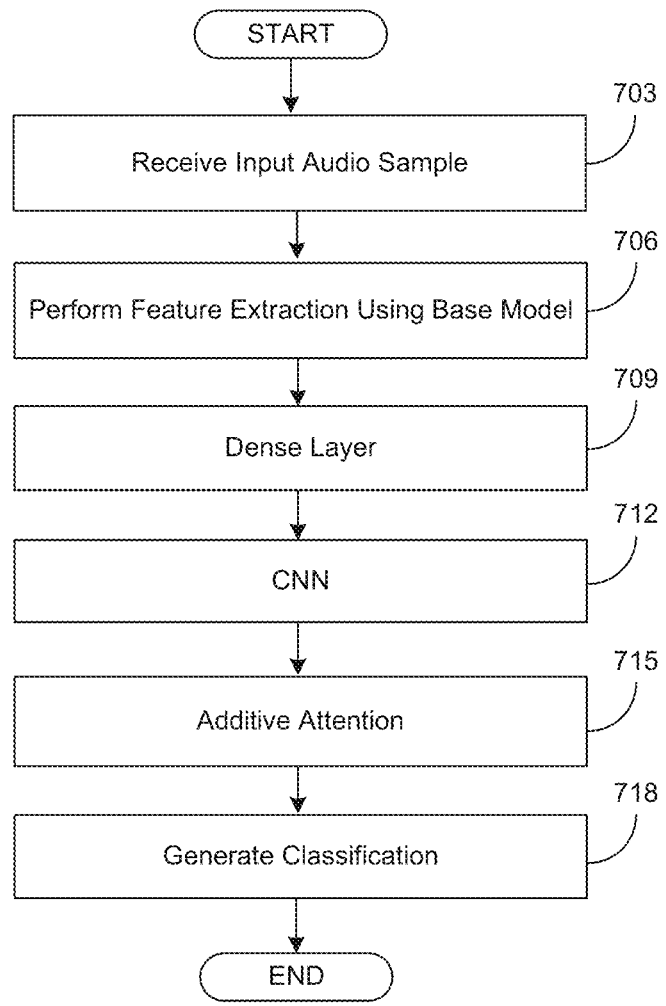
FIG. 7 is a flowchart illustrating one example of functionality as portions of a classification service and/or classification application executed in the networked environment of FIG. 1A according to various embodiments of the present disclosure.

Referring next to FIG. 7, shown is a flowchart that provides one example of the operation of a portion of the classification service 118 according to various embodiments. FIG. 7 illustrates an example of generating an emotion classification 133. In some examples, the functionality depicted in FIG. 7 can also be executed by the classification application 151 without the involvement of the computing environment 103 (e.g., the classification service 118). It is understood that the flowchart of FIG. 7 provides merely an example of the many different types of functional arrangements that may be employed to implement the operation of the portion of the classification service 118 as described herein. As an alternative, the flowchart of FIG. 7 may be viewed as depicting an example of elements of a method implemented in the computing environment 103 (FIG. 1A) according to one or more embodiments.

Beginning with box 703, the classification service 118 can receive an audio sample 139 for generating an emotion classification 133. The audio sample 139 can include an utterance of an individual, such as a therapy patient. The audio sample 139 can be captured by the classification application 151 executed on the client device 106. The classification application 151 can transmit the audio sample 139 to the classification service 118.

In box 706, the classification service 118 can use the base model 127 (e.g., via the emotion model 131) to perform feature extraction on the audio sample 139. In this example, the base model 127 has been trained to extract acoustic emotion characteristics from the audio sample 139. The output of the base model 127 can be provided to a dense layer 403.

In box 709, the classification service 118 can cause the dense layer 403 to process the output of extracted features from the base model 127. The dense layer 403 can process the extracted features in order to reduce dimensionality. The dense layer 403 can provide an output that is inputted to the CNN layer 406. In some embodiments, box 709 can be omitted. In these embodiments, the output of the base model 127 can be directed to the CNN layer 406.

In box 712, the classification service 118 can cause the CNN layer 406 to process the output of the dense layer 403. The CNN layer 406 can generate an output that is provided to the additive attention layer 409.

In box 715, the classification service 118 can cause the additive attention layer 409 to process the output from the additive attention layer 409. The additive attention layer 409 can generate an output that is provided to the classifier layer 412.

In box 718, the classification service 118 can cause the classifier layer 412 to generate a prediction for a level of emotion existing in the audio sample 139. In some embodiments, the classifier layer 412 can generate a prediction probability for each level (e.g., low, medium, high) of an emotion type (e.g., anger, fear, sadness, happiness). The classifier layer 412 can select the level that has the highest prediction probability for each emotion type. Further, in some examples, the classification service 118 can aggregate (e.g., an average) the levels (e.g., scores) for two or more emotion types. Then, the classification service 118 can proceed to completion.

Figure 8:
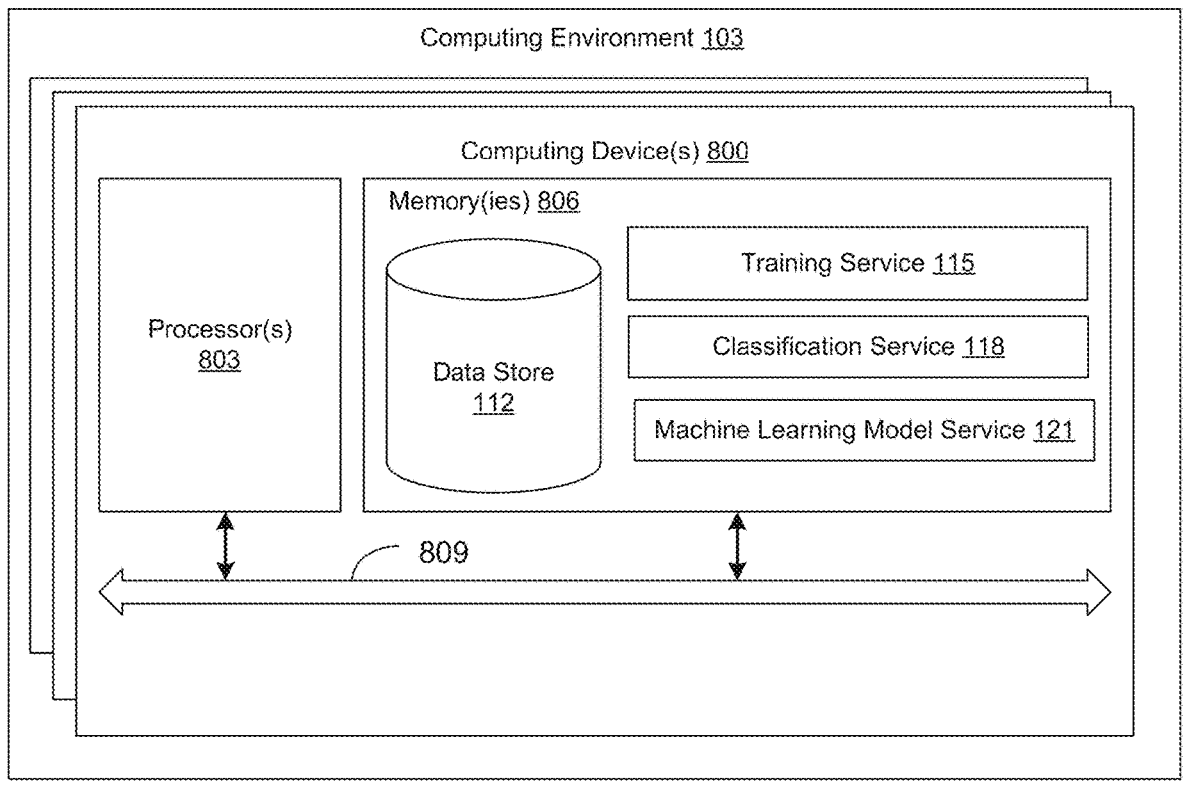
FIG. 8 is a schematic block diagram that provides one example illustration of a computing environment employed in the networked environment of FIG. 1A according to various embodiments of the present disclosure.

With reference to FIG. 8, shown is a schematic block diagram of the computing environment 103 according to an embodiment of the present disclosure. The computing environment 103 includes one or more computing devices 800. Each computing device 800 includes at least one processor circuit, for example, having a processor 803 and a memory 806, both of which are coupled to a local interface 809. To this end, each computing device 800 may comprise, for example, at least one server computer or like device. The local interface 809 may comprise, for example, a data bus with an accompanying address/control bus or other bus structure as can be appreciated.

Stored in the memory 806 are both data and several components that are executable by the processor 803. In particular, stored in the memory 806 and executable by the processor 803 are training service 115, the classification service 118, machine learning model service 121, and potentially other applications. Also stored in the memory 806 may be a data store 112 and other data. In addition, an operating system may be stored in the memory 806 and executable by the processor 803.

It is understood that there may be other applications that are stored in the memory 806 and are executable by the processor 803 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 806 and are executable by the processor 803. In this respect, the term "executable" means a program file that is in a form that can ultimately be run by the processor 803. Examples of executable programs may be, for example, a compiled program that can be translated into machine code in a format that can be loaded into a random access portion of the memory 806 and run by the processor 803, source code that may be expressed in proper format such as object code that is capable of being loaded into a random access portion of the memory 806 and executed by the processor 803, or source code that may be interpreted by another executable program to generate instructions in a random access portion of the memory 806 to be executed by the processor 803, etc. etc. An executable program may be stored in any portion or component of the memory 806 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 806 is defined herein as including both volatile and nonvolatile memory and data storage components. Volatile components are those that do not retain data values upon loss of power. Nonvolatile components are those that retain data upon a loss of power. Thus, the memory 806 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 803 may represent multiple processors 803 and/or multiple processor cores and the memory 806 may represent multiple memories 806 that operate in parallel processing circuits, respectively. In such a case, the local interface 809 may be an appropriate network that facilitates communication between any two of the multiple processors 803, between any processor 803 and any of the memories 806, or between any two of the memories 806, etc. etc. The local interface 809 may comprise additional systems designed to coordinate this communication, including, for example, performing load balancing. The processor 803 may be of electrical or of some other available construction.

Although training service 115, the classification service 118, machine learning model service 121, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. etc. Such technologies are generally well known by those skilled in the art and, consequently, are not described in detail herein.

The flowcharts of FIGS. 5-7 show the functionality and operation of an implementation of portions of the training service 115, the classification service 118, and the classification application 151. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 803 in a computer system or other system. The machine code may be converted from the source code, etc. etc. If embodied in hardware, each block may represent a circuit or a number of interconnected circuits to implement the specified logical function(s).

Although the flowcharts of FIGS. 5-7 show a specific order of execution, it is understood that the order of execution may differ from that which is depicted. For example, the order of execution of two or more blocks may be scrambled relative to the order shown. Also, two or more blocks shown in succession in FIGS. 5-7 may be executed concurrently or with partial concurrence. Further, in some embodiments, one or more of the blocks shown in FIGS. 5-7 may be skipped or omitted. In addition, any number of counters, state variables, warning semaphores, or messages might be added to the logical flow described herein, for purposes of enhanced utility, accounting, performance measurement, or providing troubleshooting aids, etc. etc. It is understood that all such variations are within the scope of the present disclosure.

Also, any logic or application described herein, including training service 115, the classification service 118, machine learning model service 121, that comprises software or code can be embodied in any non-transitory computer-readable medium for use by or in connection with an instruction execution system such as, for example, a processor 803 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including training service 115, the classification service 118, machine learning model service 121, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 800, or in multiple computing devices in the same computing environment 103. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A system for classifying a level of emotion of an audio sample, comprising:
   at least one computing device that comprises a processor and memory; and
   machine-readable instructions stored in the memory that, when executed by the processor, cause the at least one computing device to at least:
   receive an audio sample that includes an utterance of a user;
   perform a feature extraction on the audio sample to extract a plurality of acoustic emotion features using a base model, the base model comprising a convolution neutral network (CNN) layer, a Densenet model, and a transformer layer, the base model using the CNN layer to extract an initial set of emotion features from the audio sample, the CNN layer providing the initial set of emotion features to the Densenet model, the Densenet model identifying a set of learned features and passing the set of learned features through a plurality of skip connections to the transformer layer, the transformer layer generating the plurality of acoustic emotion features based at least in part on learning a plurality of relationships between a plurality of component parts of the utterance;
   generate a plurality of emotion level predictions for a first emotion type and a second emotion type based at least in part on the plurality of acoustic emotion features being provided to a first emotion specific model and a emotion specific model, the first emotion specific model comprising a first emotion specific CNN and being trained to identify a first level of the first emotion type, the second emotion specific model comprising a second emotion specific CNN and being trained to identify a second level of the second emotion type; and determine a level of emotional distress severity represented in the audio sample based at least in part on the first level for the first emotion type and the second level for the second emotion type.

2. The system of claim 1, wherein the base model is a machine learning model that is trained in an unsupervised manner using a temporal proximity as a metric to evaluate a loss function of the base model.

3. The system of claim 1, wherein the CNN layer comprises a plurality of CNN layers, and at least some of the plurality of skip connections skip at least one respective CNN layer in an ordered arrangement of the plurality of CNN layers.

4. The system of claim 3, wherein at least some of the plurality of skip connections skip the at least one respective CNN layer and feed an output of a first CNN layer to a second CNN layer.

5. The system of claim 1, wherein and the machine-readable instructions, when executed by the processor, cause the at least one computing device to at least:

generate an aggregate emotion score for the audio sample based at least in part on the first emotion type, the first level, the second emotion type, and the second level associated with the second emotion type.

6. The system of claim 1, wherein the first emotion specific model comprises an additive attention layer and a classifier.

7. A method, comprising:

receiving, by at least one computing device, an audio sample that includes an utterance of a user;

performing, by the at least one computing device, a feature extraction on the audio sample to extract a plurality of acoustic emotion features using a base model, the base model comprising a convolution neutral network (CNN) layer, a Densenet model, and a transformer layer, the base model using the CNN layer to extract an initial set of emotion features from the audio sample, the CNN layer providing the initial set of emotion features to the Densenet model, the Densenet model identifying a set of learned features and passing the set of learned features through a plurality of skip connections to the transformer layer, the transformer layer generating the plurality of acoustic emotion features based at least in part on learning a plurality of relationships between a plurality of component parts of the utterance;

generating, by the at least one computing device, a plurality of emotion level predictions for a first emotion type and a second emotion type based at least in part on the plurality of acoustic emotion features being provided to a first emotion specific model and a second emotion specific model, the first emotion specific model comprising a first emotion specific CNN and being trained to identify a first level of the first emotion type, the second emotion specific model comprising a second emotion specific CNN and being trained to identify a second level of the second emotion type; and determining, by the at least one computing device, a level of emotional distress severity represented in the audio sample based at least in part on the first level for the first emotion type and the second level for the second emotion type.

8. The method of claim 7, wherein the base model is a machine learning model that is trained in an unsupervised manner using a temporal proximity as a metric to evaluate a loss function of the base model.

9. The method of claim 7, wherein the first emotion type comprises at least one of anger, happiness, fear, or sadness.

10. The method of claim 7, wherein the CNN layer comprises a plurality of CNN layers, and at least some of the plurality of skip connections that skip at least one respective CNN layer in an ordered arrangement of the plurality of CNN layers.

11. The method of claim 10, wherein the at least some of the plurality of skip connections skip the at least one respective CNN layer and feed an output of a first CNN layer to a second CNN layer.

12. The method of claim 7, further comprising:

generating, by the at least one computing device, an aggregate emotion score for the audio sample based at least in part on the first emotion type, the first level, the second emotion type, and the second level associated with the second emotion type.

13. The method of claim 7, wherein the first emotion specific model comprises an additive attention layer and a classifier.

14. A system, comprising:

at least one computing device; and machine-readable instructions stored in memory that, when executed, cause the at least one computing device to at least:

receive an audio sample that includes an utterance of a user, the audio sample comprises a label, the label comprising an emotion level for a particular emotion type;

perform a feature extraction on the audio sample to extract a plurality of acoustic emotion features using a base model, the base model comprising a convolution neutral network (CNN) layer, a Densenet model, and a transformer layer, the base model using the CNN layer to extract an initial set of emotion features from the audio sample, the CNN layer providing the initial set of emotion features to the Densenet model, the Densenet model identifying a set of learned features and passing the set of learned features through a plurality of skip connections to the transformer layer, the transformer layer generating the plurality of acoustic emotion features based at least in part on learning a plurality of relationships between a plurality of component parts of the utterance;

generate a plurality of emotion level predictions for a first emotion type and a second emotion type based at least in part on the plurality of acoustic emotion features being provided to a first emotion specific model and a second emotion specific model, the first emotion specific model comprising a first emotion specific CNN and being trained to identify a first level of the first emotion type, the second emotion specific model comprising a second emotion specific CNN and being trained to identify a second level of the second emotion type;

determine an emotion classification for the audio sample based at least in part on the first level for the first emotion type and the second level for the second emotion type; and update a parameter associated with the first emotion specific model or the second emotion specific model based at least in part on a comparison between the emotion classification and the label of the audio sample.

15. The system of claim 14, wherein the parameter is associated with a respective CNN for the first emotion specific model.

16. The system of claim 14, wherein the first emotion specific model comprises an additive attention layer and a classifier.

17. The system of claim 16, wherein the CNN layer comprises a plurality of CNN layers, and at least some of the plurality of skip connections skip at least one respective CNN layer in an ordered arrangement of the plurality of CNN layers.

18. The system of claim 17, wherein the at least some of the plurality of skip connections skip the at least one respective CNN layer and feed an output of a first CNN layer to a second CNN layer.

* * * * *